United States Patent [19]

Giordano et al.

[11] Patent Number: 5,630,832
[45] Date of Patent: May 20, 1997

[54] TUBULAR-SHAFTED SURGICAL INSTRUMENT

[75] Inventors: Nicola Giordano, Villingen-Schwenningen; Pedro Morales; Markus Nesper, both of Tuttlingen; Lino Taddia, Wurmlingen; Dieter Weisshaupt, Immendingen, all of Germany

[73] Assignee: Aesculap AG, Tuttlingen, Germany

[21] Appl. No.: 656,252

[22] PCT Filed: Oct. 6, 1994

[86] PCT No.: PCT/EP94/03308

§ 371 Date: Jul. 3, 1996

§ 102(e) Date: Jul. 3, 1996

[87] PCT Pub. No.: WO95/15720

PCT Pub. Date: Jun. 15, 1995

[30] Foreign Application Priority Data

Dec. 8, 1993 [DE] Germany ............... 43 41 736.1

[51] Int. Cl.$^6$ ............................................. A61B 17/28
[52] U.S. Cl. .................... 606/208; 606/207; 606/170
[58] Field of Search .......................... 606/205, 206, 606/207, 208, 127, 167; 128/751

[56] References Cited

U.S. PATENT DOCUMENTS

| | | |
|---|---|---|
| 4,944,741 | 7/1990 | Hasson . |
| 5,152,779 | 10/1992 | Sanagi . |
| 5,350,391 | 9/1994 | Iacovelli ........................ 606/170 |
| 5,368,606 | 11/1994 | Marlow et al. ................. 606/207 |

FOREIGN PATENT DOCUMENTS

| | | |
|---|---|---|
| 0513471 | 11/1992 | European Pat. Off. . |
| 3934610 | 4/1991 | Germany . |
| 9007356 | 6/1991 | Germany . |
| 9202132 | 6/1992 | Germany . |
| 2140735 | 12/1984 | United Kingdom . |
| WO91/05514 | 5/1991 | WIPO . |

*Primary Examiner*—Michael Buiz
*Assistant Examiner*—Kevin Truong
*Attorney, Agent, or Firm*—Barry R. Lipsitz

[57] ABSTRACT

A tubular-handled surgical instrument has two mutually articulated grip shanks. A tube is secured on one of the shanks, with a tool fitted at its end. A rod-like actuator for the tool is fitted to move longitudinally in the tube and articulated on the other shank via a cylindrical or spherical end. A releasable connection is provided between the tube and the actuator on the one hand and between the two shanks on the other. The tube is insertable into a tubular recess in one shank and axially securable therein by at least one radially movable spherical locking member making a friction fit with the tube in one end position. The radial movement of the locking member is limited by a stop bearing on the outside of the locking member formed by a sleeve axially movable on the tubular recess. The sleeve is movable in relation to the locking member in such a way that the locking member can be moved radially outwards to differing extents.

18 Claims, 7 Drawing Sheets

TUBULAR-SHAFTED SURGICAL INSTRUMENT

BACKGROUND OF THE INVENTION

The invention relates to a tubular-shafted surgical instrument comprising two handle parts articulatedly connected to each other, a tube held on one handle part, a tool mounted at the end of the tube, a rod-shaped actuating element for the tool, the actuating element being mounted for longitudinal displacement in the tube and being articulatedly connected to the other handle part via a cylindrical or spherical end, and a releasable connection between tube and actuating element, on the one hand, and the two handle parts, on the other hand, the tube being pushable into a tubular receptacle on the one handle part and axially fixable therein by at least one radially moveable locking body which in an end position enters into a positive connection with the tube, and a retaining member being mounted on the other handle part, the retaining member partly embracing the cylindrical or spherical end of the actuating element in one end position and being moveable into another end position in which the cylindrical or spherical end is removable from the other handle part in the longitudinal direction.

In tubular-shafted instruments of this kind (GB 2 140 735 A), which can be employed in a wide variety of ways, it is important to be able to disassemble the instrument as completely as possible for the purposes of tool exchange and cleaning.

Instruments of this kind, wherein the handle parts can be connected to the tube and to the actuating element via threaded connections, are known. The making and releasing of the connection take a relatively long time as fine threads, which require a large number of turnings, normally have to be used. It is also difficult to connect the concentric parts simultaneously in this way, as two different connections have to be made.

Surgical instruments of the kind described at the outset are already on offer (AESCULAP Main Catalog, 1991 edition, page 647). It is, however, necessary to provide a separate radially protruding part for the fixing, which, under certain circumstances, can complicate the making and releasing of the connection.

The object of the invention is to so design a generic instrument that the making and releasing of the connection between tube and actuating element, on the one hand, and the handle parts, on the other hand, is facilitated, and, in addition, locking and unlocking of the releasable mounting of the tool are also to be facilitated.

SUMMARY OF THE INVENTION

This object is accomplished in accordance with the invention in a surgical instrument of the kind described at the outset by the locking body being a ball, by the radial movement of the locking body being delimited by a stop resting against the outer side of the locking body, the stop being formed by a sleeve axially displaceable on the tubular receptacle, by the sleeve being displaceable relative to the locking body such that the locking body is radially outwardly displaceable to different extents, [locking body . . . radially . . . to different extents], by the sleeve forming a stop for an outer tube which is mounted for axial displacement on the tube and in the pushed forward end position locks the releasable mounting of the tool at the opposite end of the tube, and by the sleeve being displaceable in the direction towards the handle parts in order to release the locking of the tube.

Accordingly, separate, displaceable closure elements which can each be displaced or turned by a movement between a closed position and an open position are used for both the tube and the actuating element, and so the releasing and connecting are very easily effected. In particular, these operations can be carried out very quickly.

The design of the locking of the tube in the one handle part as ball locking mechanism facilitates the making and also the releasing of this connection quite considerably. Ball locking mechanisms are known per se as quick coupling for surgical instruments (WO 91/05514), but these known quick couplings are mainly employed for connecting surgical instruments to holders or extensions. It is not known from the aforementioned publication to use a ball locking mechanism for connecting the shaft of a tubular-shafted instrument to a handle part.

To release the tube from the receptacle it is sufficient to displace the sleeve on the tubular receptacle into an end position, and the locking body can then release the tube in the radial direction. The sleeve displaceable on the tubular receptacle not only fixes the locking body which fixes the tube in the tubular receptacle, but also an outer tube on the tube, and the outer tube, in turn, forms at the front end of the tube a lock for an exchangeable tool.

It is advantageous for the sleeve to be moved in a spring-loaded manner into the end position in which the path of displacement of the locking body is limited to the greatest extent. The spring thus always displaces the sleeve into the locking position. Only against the force of this spring is release of the axial fixing of the tube in the receptacle possible.

In another embodiment, provision may be made for the tubular receptacle to form a stop for an outer tube which is mounted for axial displacement on the tube and in the pushed forward end position locks the releasable mounting of the tool at the opposite end of the tube. In this embodiment, the outer tube can only be displaced on the tube when the tube is pulled out of the tubular receptacle, i.e., in order to exchange the tool, the entire instrument must first be separated.

It is expedient for the tube to be secured against rotation about the longitudinal axis of the tube by engagement of projections and recesses when it is pushed into the tubular receptacle. A defined position of the tool plane is thus attainable. Provision may be made for projections and recesses to [engage in different angular positions], and by briefly separating the tube from the instrument, the operator can thus selectively turn the tube to different angular positions and fix it in these.

In a modified embodiment, provision may also be made for the tubular receptacle to be mounted for rotation about its longitudinal axis on the handle part. By turning this tubular receptacle, the tube with the tool mounted thereon can be turned to the desired position and so the operator is completely free in the angular positioning of the tool.

In a first preferred embodiment, provision may be made for the retaining member to be constructed as a collet chuck which in the released state allows entry or exit of the spherical or cylindrical end by bending open elastically and in the closed state embraces the spherical or cylindrical end unreleasably. Such a collet chuck can be locked by, for example, axial pushing into a sleeve. If desired, this pushing-in can be effected by a threaded nut.

In another embodiment, provision is made for the retaining member to be mounted for swivel movement on the other handle part and to engage in the closed state in a section of the actuating element adjacent to the spherical or cylindrical end, the outer dimensions of the section transversely to the longitudinal direction of the actuating element being smaller than those of the spherical or cylindrical end. To release the rotary connection between actuating element, on the one hand, and handle part, on the other hand, it is, therefore, sufficient to swivel the retaining member on the handle part, i.e., one manual maneuver suffices to selectively attain the closed state or the released state.

It is particularly advantageous for the retaining member to have a receiving space for the spherical or cylindrical end with an opening which has a larger region sufficient for passage of the spherical or cylindrical end therethrough, and a smaller region which is too narrow for passage therethrough, and for the two regions to be selectively moveable in the longitudinal direction of the actuating element in front of its spherical or cylindrical end by movement of the retaining member. The receiving space encloses the spherical or cylindrical end and thereby reliably transmits both pulling and pushing movements. Solely by swivelling the retaining member, it is possible to release the actuating element, namely when the larger region of the opening is oriented in the longitudinal direction of the actuating element.

It is expedient for the actuating member to be positionable in its end positions by elastic detent members.

In particular, the opening of the receiving space can be of keyhole-shaped design.

DESCRIPTION OF THE DRAWINGS

The following description of preferred embodiments serves in conjunction with the drawings to explain the invention in further detail. The drawings show.

DESCRIPTION OF THE PREFERRED EMBODIMENTS

Figure 1:
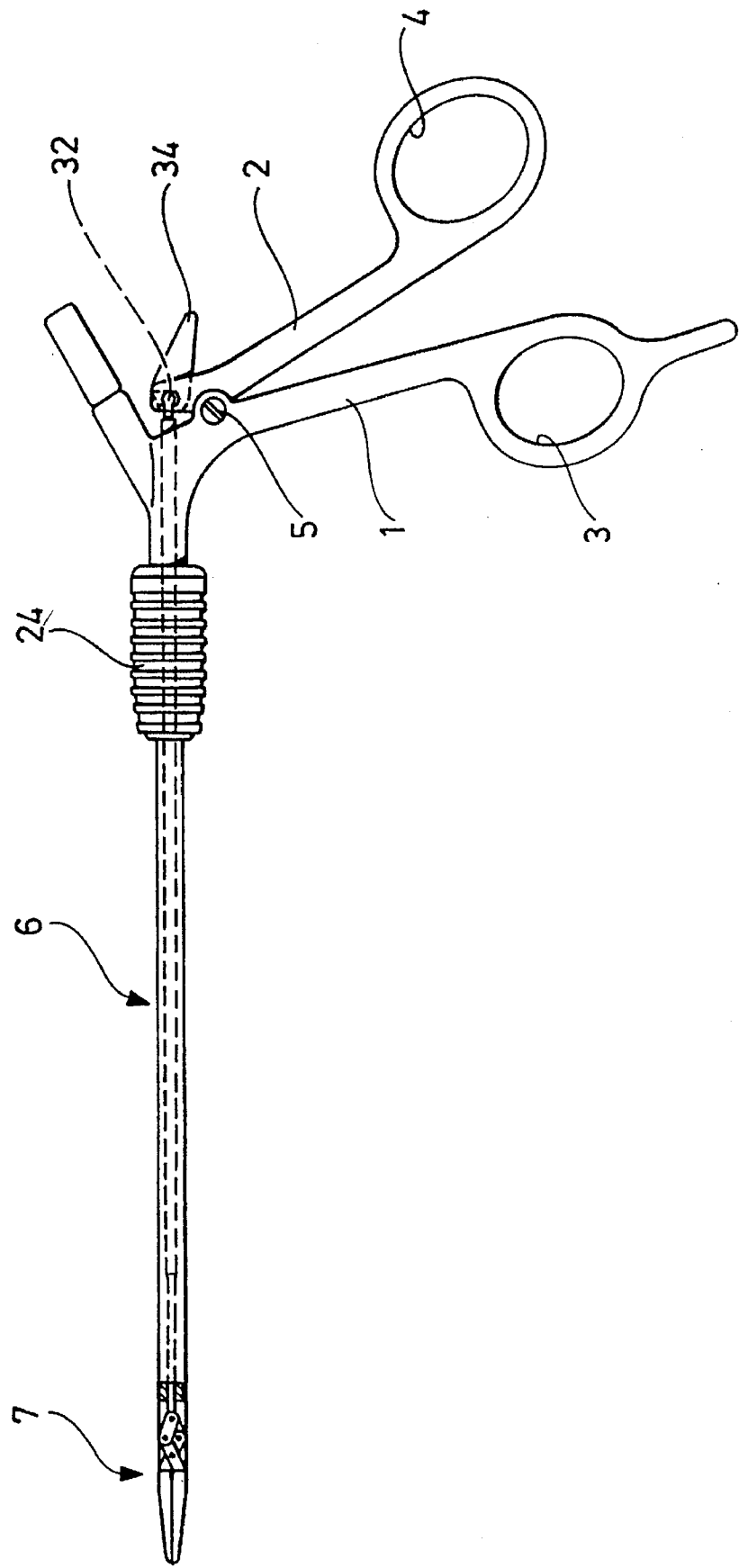
FIG. 1 a side view of a tubular-shafted instrument which can be disassembled.

The tubular-shafted instrument illustrated in the drawings comprises two handle parts 1 and 2 which are pivotably connected to each other and each have a finger opening 3 and 4, respectively. The two handle parts 1 and 2 are pivotably connected to each other by a screw connection 5. Held on a handle part 1 is a shaft 6 having located at the free end thereof a tool 7 which can be in the form of, for example, scissors or forceps. Arranged for longitudinal displacement in the interior of the shaft 6 is a rod-shaped actuating element 8 which is articulatedly connected, on the one hand, to the tool 7, and, on the other hand, to the other handle part 2 so that during opening and closing of the handle parts 1 and 2, the tool 7 can be opened and closed by a pulling or pushing movement of the actuating element 8.

Figure 2:
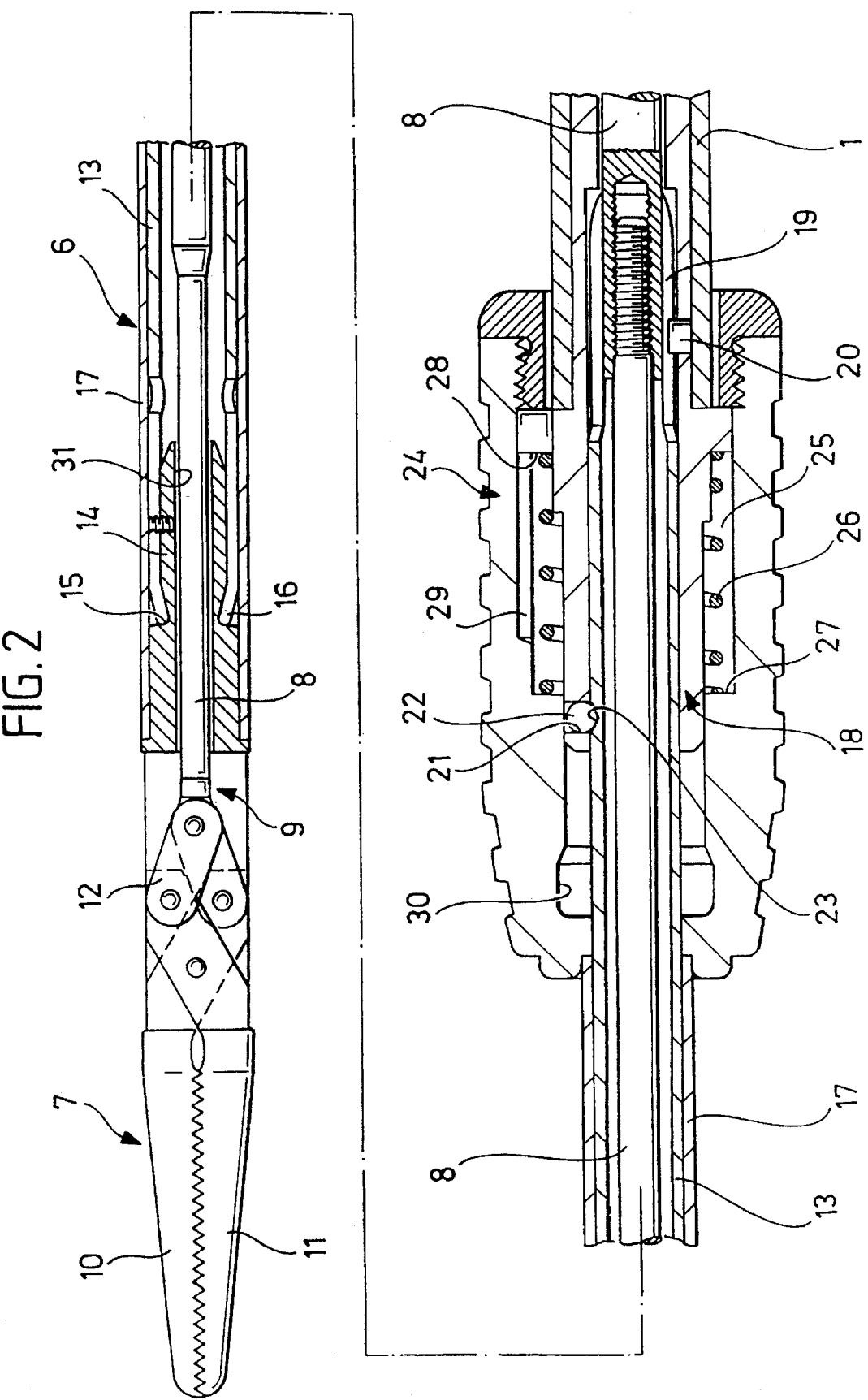
FIG. 2 a longitudinal sectional view of the front part and the central part of the tubular-shafted instrument of FIG. 1.
Figure 3:
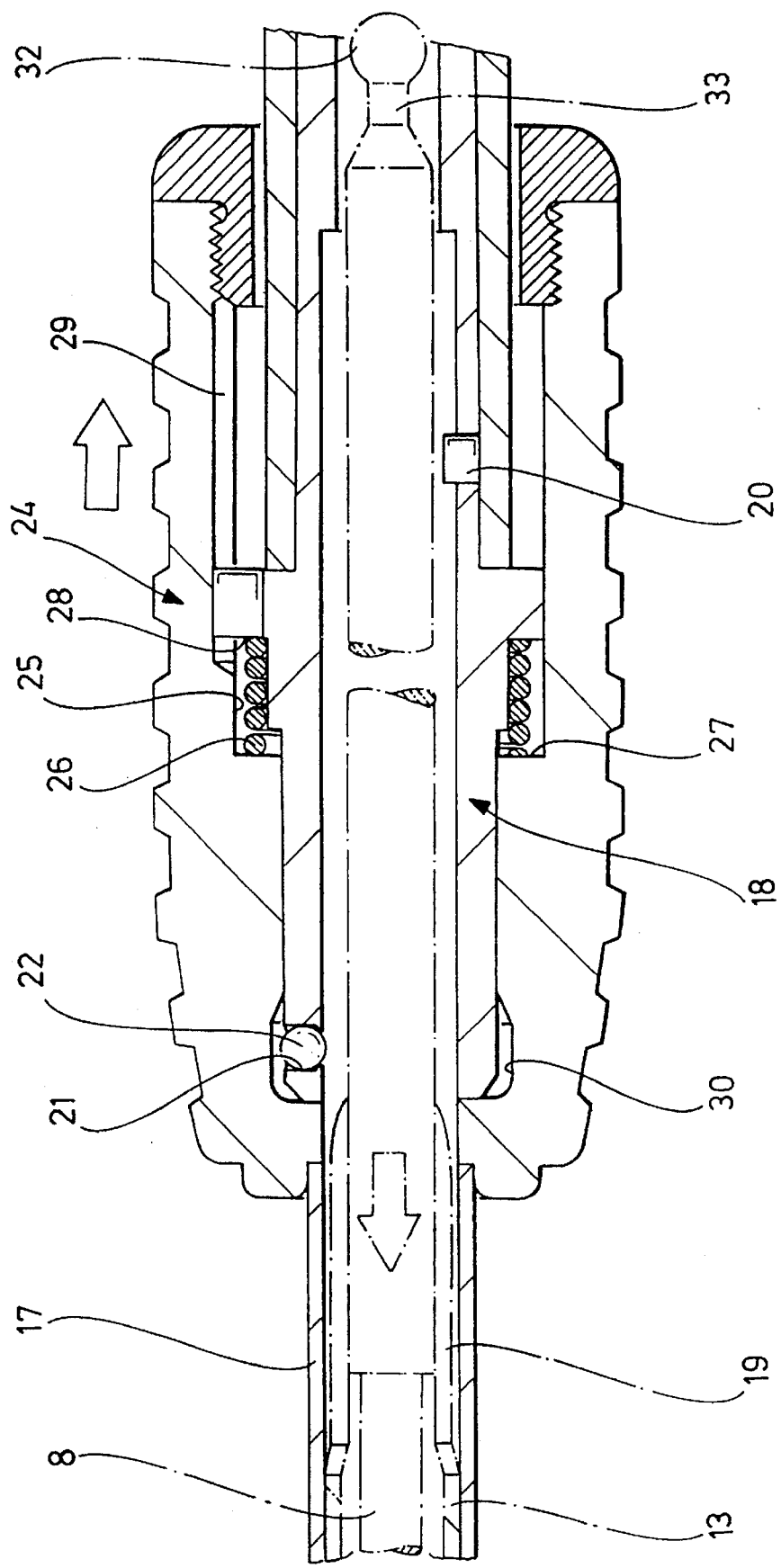
FIG. 3 an enlarged longitudinal sectional view of the central part of the tubular-shafted instrument of FIG. 1 in the unlocked state.

In the illustrated embodiment, this tool 7 comprises two parts 10, 11, which are rotatably mounted on a holder 9 and are pivotably connected to the actuating element 8 via gear means 12 (FIG. 2). This holder 9 is releasably connected to a tube 13. For this purpose, the holder 9 carries an extension 14 which reaches into the tube 13 and has a circumferential groove 15. At its free end, the tube 13 is divided up by longitudinal slots into tongues 16 which can bend open elastically and at their free end are bent inwardly. These tongues 16 surround the extension 14 and reach with their bent end into the circumferential groove 15 so that the extension 14 is fixed in the axial direction in the tube 6. The tongues 16 are held permanently in this position by an outer tube 17 which is longitudinally displaceable on the tube 13 being pushed over the tongues 16 so that the tongues 16 are prevented from moving radially outwardly. The outer tube 17 thus forms a lock which can only be released when the outer tube 17 is pushed back over the tongues 16.

The tube 13 and the outer tube 17 displaceably mounted thereon together form the shaft 6 which can be releasably connected to the handle part 1. To this end, this handle part 1 carries a tubular receptacle 18 which, if desired, may be rotatable relative to the handle part 1 about the longitudinal axis of the receptacle 18. Insertable into this receptacle 18 is the tube 13, the outer diameter of which corresponds to the inner diameter of the receptacle 18. At its end pushed into the receptacle 18, the tube 13 has longitudinal slots 19 into which a projection 20 held in the tubular receptacle 18 protrudes.

The tube 13 is thereby non-rotatably mounted in the receptacle 18. Several longitudinal slots may be provided so that the tube 13 can be fixed in different angular positions in the receptacle 18.

Mounted in a radial bore 21 of the tubular receptacle 18 in the form of a ball is a locking member 22 which extends into a recess 23 in the outer jacket of the tube 13 when the tube 13 is pushed into the receptacle 18. In a way which is not apparent from the drawings, the radial bore 21 is of not quite continuous construction on the inner side so that even when the tube 13 is missing, the ball 22 cannot fall radially inwardly out of the radial bore 21. Outwardly, however, the radial bore 21 is of continuous construction so the ball 22 is freely moveable radially outwardly.

A sleeve 24 surrounding the receptacle 18 is mounted for displacement in the longitudinal direction on the tubular receptacle 18. In an annular space 25 located between the sleeve 24 and the receptacle 18, the sleeve 24 surrounds a helical spring 26. The latter is supported, on the one hand, on a step 27 of the sleeve 24, and, on the other hand, on a step 28 of the receptacle 18 and thus acts upon the sleeve 24 with a force which displaces it in the direction of the tool 7. The step 28 is guided in a longitudinal groove 29 of the sleeve 24 so the sleeve 24 is thereby secured against rotation relative to the receptacle 18.

The movement of the sleeve 24 in the direction towards the tool 7 is delimited by the sleeve 24 striking the outer tube 17 and thus displacing the latter into its foremost position in which the tongues 16 are locked (FIG. 2). Therefore, only when the sleeve 24 is pushed back against the action of the helical spring 26 can the outer tube 17 be pushed back so far that the holder 9 can be pulled out of the tube 13.

It is also possible for the sleeve 24 to be permanently connected to the outer tube 17. Exchange of the tool 7 is then only possible when the tube 13 has been pulled out of the receptacle 18.

In an embodiment not illustrated in the drawings, provision could also be made for the outer tube 17 to strike the receptacle 18. In this case, too, for displacement of the outer tube 17, it would be necessary to pull the tube 6 out of the receptacle 18. In this case, the movement of the sleeve 24 could be delimited by another suitable stop.

The sleeve 24 rests with its inner wall against the outer side of the receptacle 18 such that the radial bore 21 is closed and so when the helical spring 26 is relaxed, movement of the ball 22 radially outwardly is prevented. The dimensions are such that in this case the ball 22 reaches into the recess 23.

When the sleeve 24 is pushed into an open position, with the helical spring 26 being compressed, a circumferential groove 30 on the inner side of the sleeve 24 is moved over the radial bore 21 so that the ball 22 is then radially outwardly displaceable to a limited extent in the radial bore 21, more specifically, to the extent that the ball 22 emerges completely from the recess 23. In this position, the axial fixing of the tube 13 in the receptacle 18 which is brought about by the ball 22 is released, and, therefore, in this position, the tube 13 can be pulled out of the receptacle 18.

The rod-shaped actuating element 8 extends through a central bore 31 of the extension 14 and protrudes rearwardly beyond the tube 13, more specifically, to the extent that it also protrudes from the handle part 1. In this region, the rod-shaped actuating element 8 carries a spherical end 32 which is connected to the actuating element 8 by a connecting section 33 with a smaller outer diameter.

The spherical end 32 forms an articulated connection with the second handle part 2.

Figure 4:
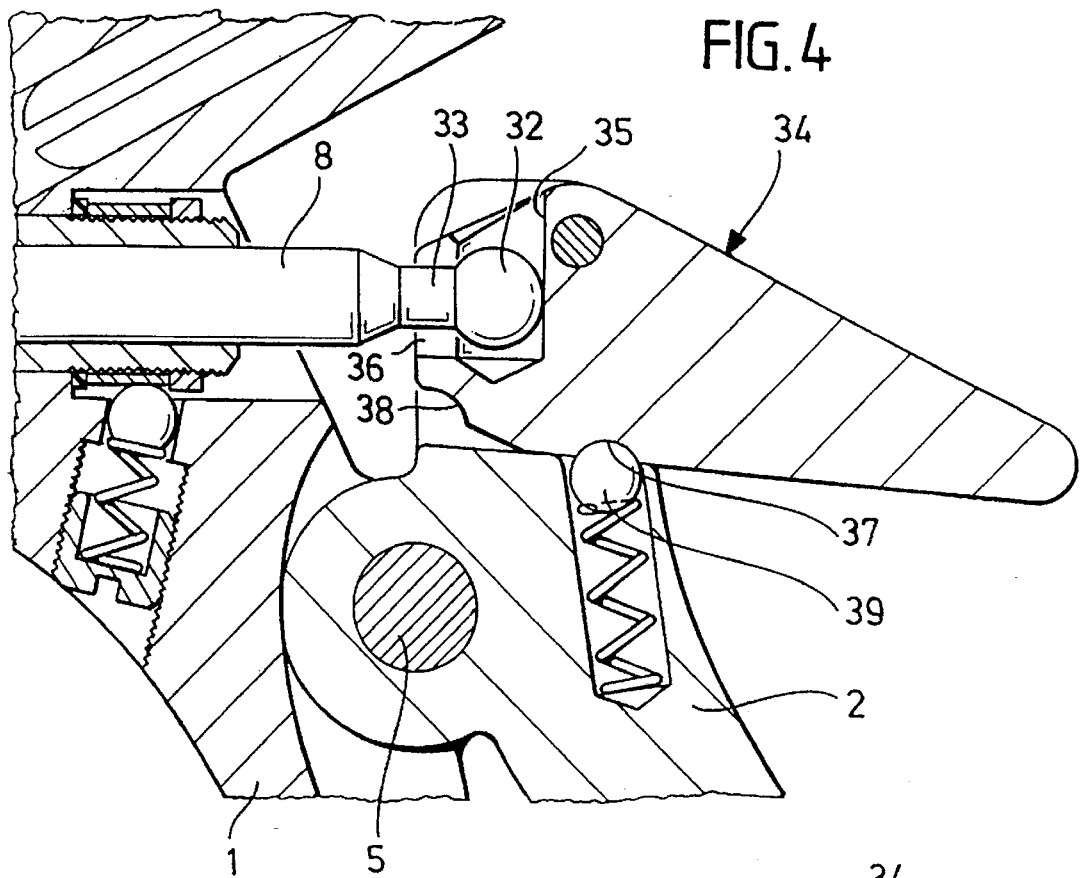
FIG. 4 a longitudinal sectional view of the tubular-shafted instrument of FIG. 1 in the region of the releasable mounting of the actuating element on the handle part with the retaining member locked.
Figure 5:
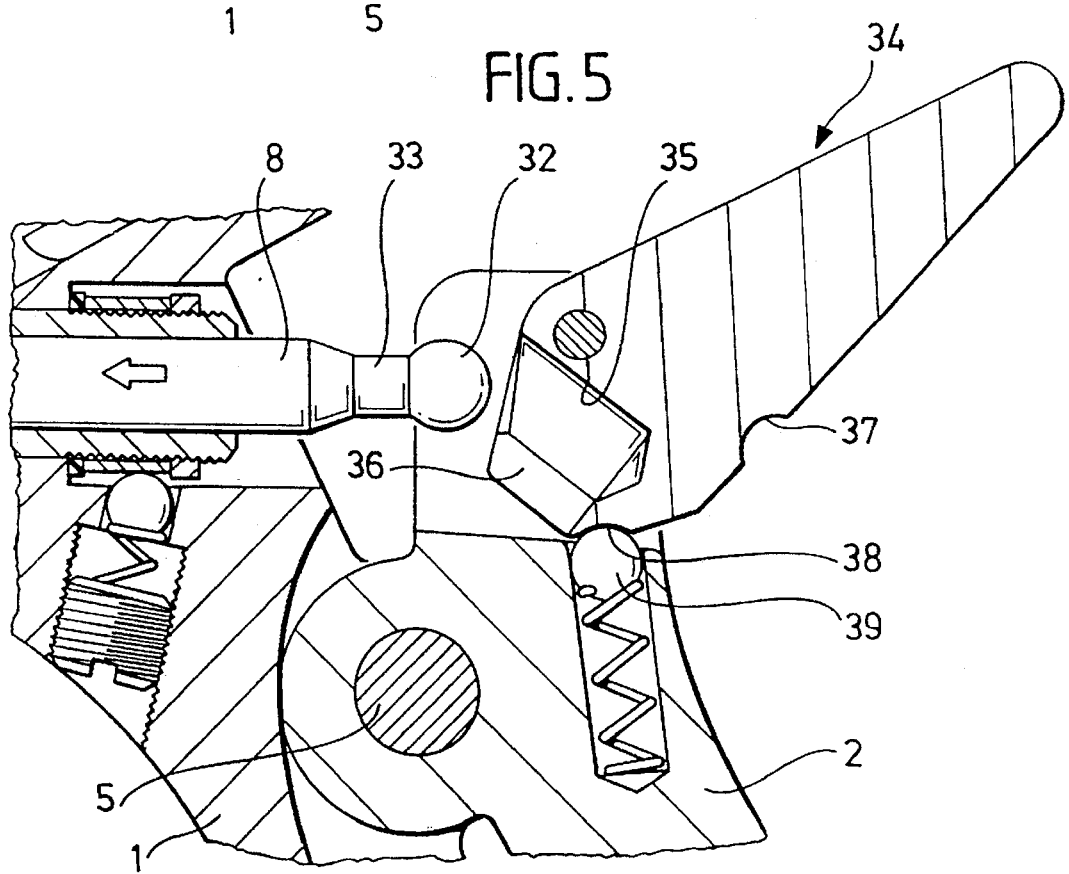
FIG. 5 a view similar to FIG. 4 with the retaining member open.

For this purpose, in a first embodiment described in FIGS. 4 and 5, a swivel lever 34 is mounted on the handle part 2 for swivel movement about a horizontal axis extending transversely to the longitudinal direction of the actuating element 8. The swivel lever 34 has a blind hole bore 35 which is open on one side thereof and communicates with the environment via a longitudinal slot 36 extending parallel to its longitudinal direction. The diameter of the blind hole bore 35 corresponds essentially to the outer diameter of the spherical end 32, the width of the longitudinal slot 36 is chosen smaller and corresponds essentially to the diameter of the actuating element 8 in the narrower connecting section 33. The swivel lever 34 can be swivelled between a closed position (FIG. 4) and an open position (FIG. 5) and is fixed in both end positions by a ball 39 which engages resiliently in recesses 37 and 38, respectively. In the closed position, the spherical end 32 is received in the blind hole bore 35. This blind hole bore 35 thus forms a receiving space for the spherical end 32. In this position of the swivel lever 34, the blind hole bore 35 is upwardly open, i.e., perpendicular to the longitudinal direction of the actuating element 8 so that it is impossible to pull out the actuating element towards the front side of the instrument.

In the open position illustrated in FIG. 5, the open end of the blind hole bore 35 points in the direction of the actuating element 8 and so the latter can be pulled out of the instrument in the direction of the arrow indicated in FIG. 5. In this embodiment, the fixing of the actuating element is brought about solely by swivelling the swivel lever 34, which thus assumes the function of a retaining member for the actuating element 8.

Figure 6:
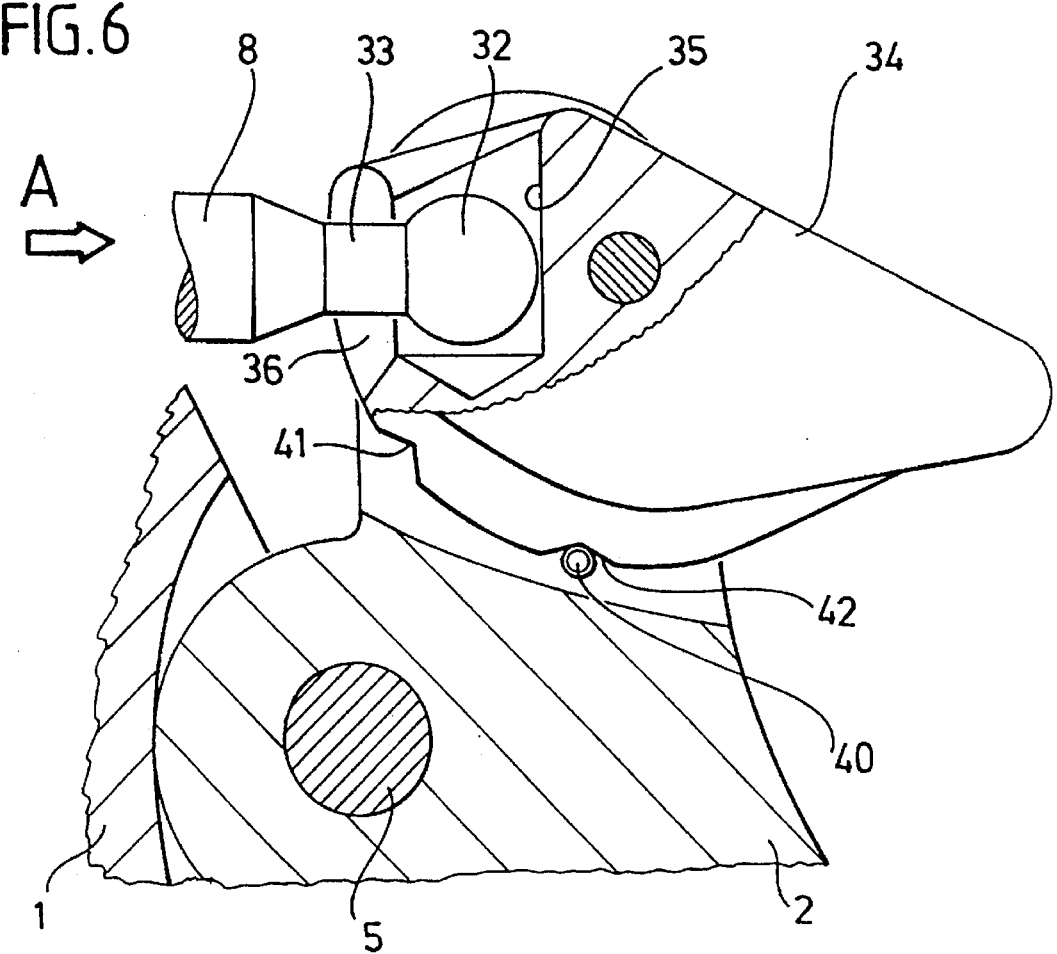
FIG. 6 a view similar to FIG. 4 of a modified embodiment of a retaining member in the closed state.
Figure 7:
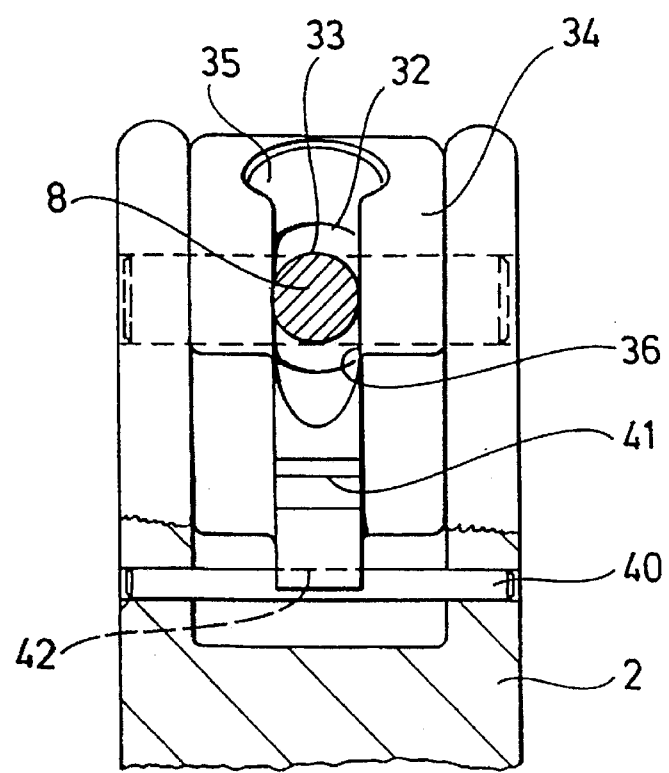
FIG. 7 a view of the retaining member in the direction of arrow A in FIG. 6.

In the embodiment of FIGS. 6 and 7, a very similar solution is illustrated, and, therefore, like parts bear the same reference numerals. In this case, the swivel lever 34 is not fixed in the end positions by a spring-loaded ball, but by a holding pin 40 which snaps resiliently into notches 41, 42 of the swivel lever 34. Herein, the elasticity of the material used for the swivel lever can be sufficient to allow the necessary displacements.

Figure 8:
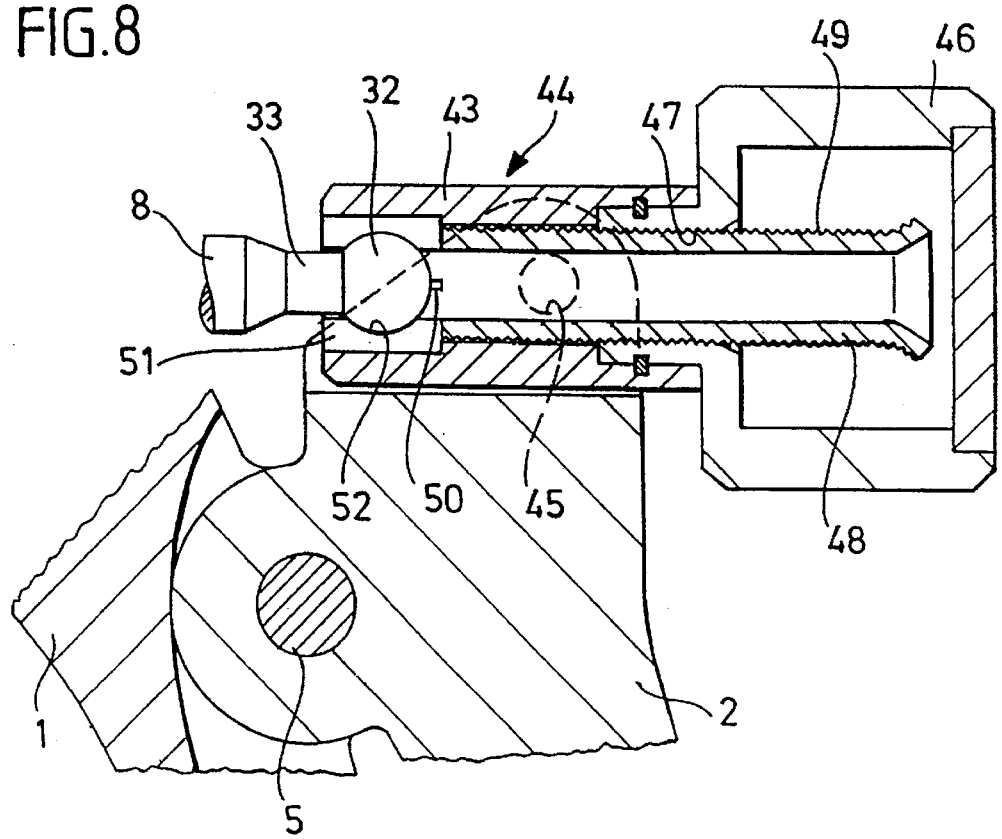
FIG. 8 a view similar to FIG. 4 of a retaining member in the form of a collet chuck in the closed state.
Figure 9:
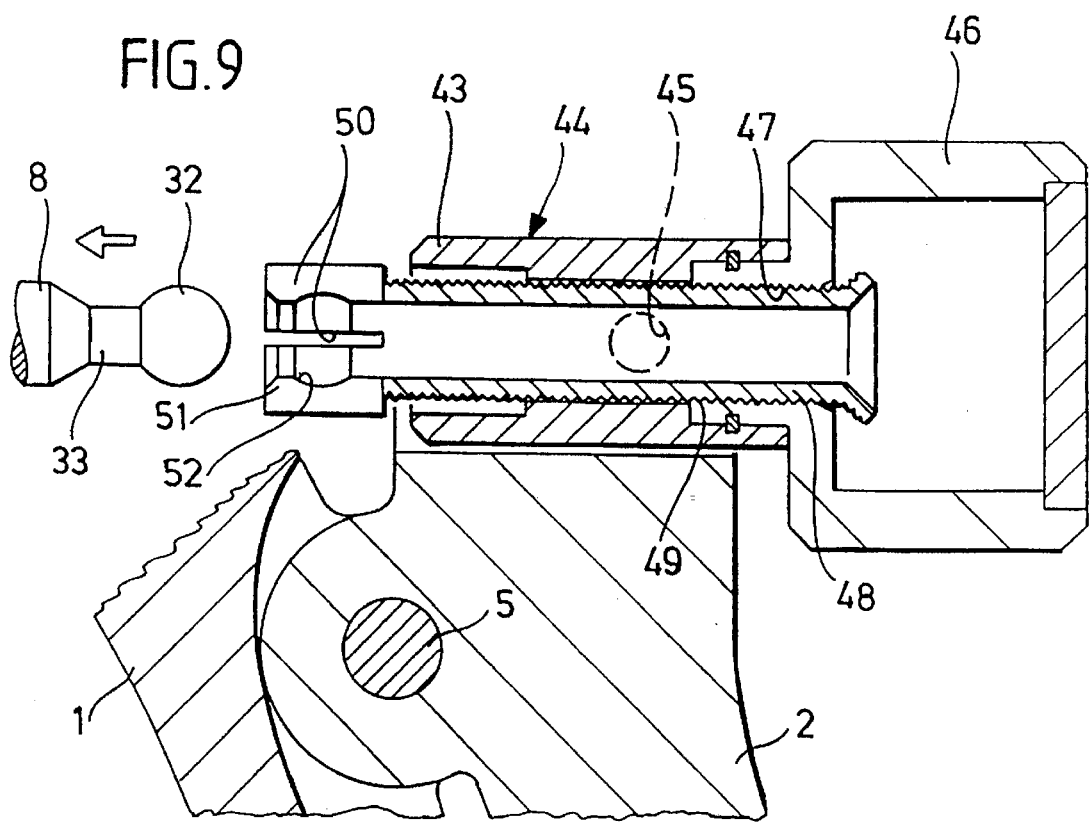
FIG. 9 a view similar to FIG. 8 with the collet chuck in the open state.

In the embodiment of FIGS. 8 and 9, a collet chuck 44 is mounted on the handle part 2 for swivel movement about a horizontal axis 45 arranged transversely to the longitudinal axis of the actuating element 8. This collet chuck 44 comprises a bearing sleeve 43 and an internally threaded sleeve 47 which is mounted so as to be rotatable but axially immoveable in the bearing sleeve 43 and has a gripping part 46. In the internally threaded sleeve 47 a tube section 48 is screwed into an external thread 49 which is pulled more or less deeply into the bearing sleeve 43 when the gripping part 46 is rotated. At the free end of the tube section 48, regions 51 which are elastically bendable radially outwardly are formed by longitudinal slots 50 and surround a spherical cap-shaped receiving space 52, the dimensions of which correspond to the outer dimensions of the spherical end 32 of the actuating element 8. When the regions 51 bend open elastically, the spherical end 32 can be pushed into the spherical cap-shaped receiving space 52 so that the regions 51 partly embrace the spherical end 32 articulatedly.

This connection is releasable again at any time so long as the regions 51 are elastically bendable outwardly, as illustrated in FIG. 9. However, by turning the gripping part 46, the internally threaded sleeve 47 can be pulled so far into the bearing sleeve 43 that the elastic regions 51 rest against the inner side of the bearing sleeve 43 and are thereby prevented from elastic deformation outwardly. This is illustrated in FIG. 8. The spherical end 32 is thereby unreleasably but articulatedly fixed in the receiving space 52. To release this connection it is sufficient to turn the gripping part 46 in order to push the internally threaded sleeve 47 so far out of the bearing sleeve 43 again that the elastic regions 51 are outwardly bendable.

Figure 10:
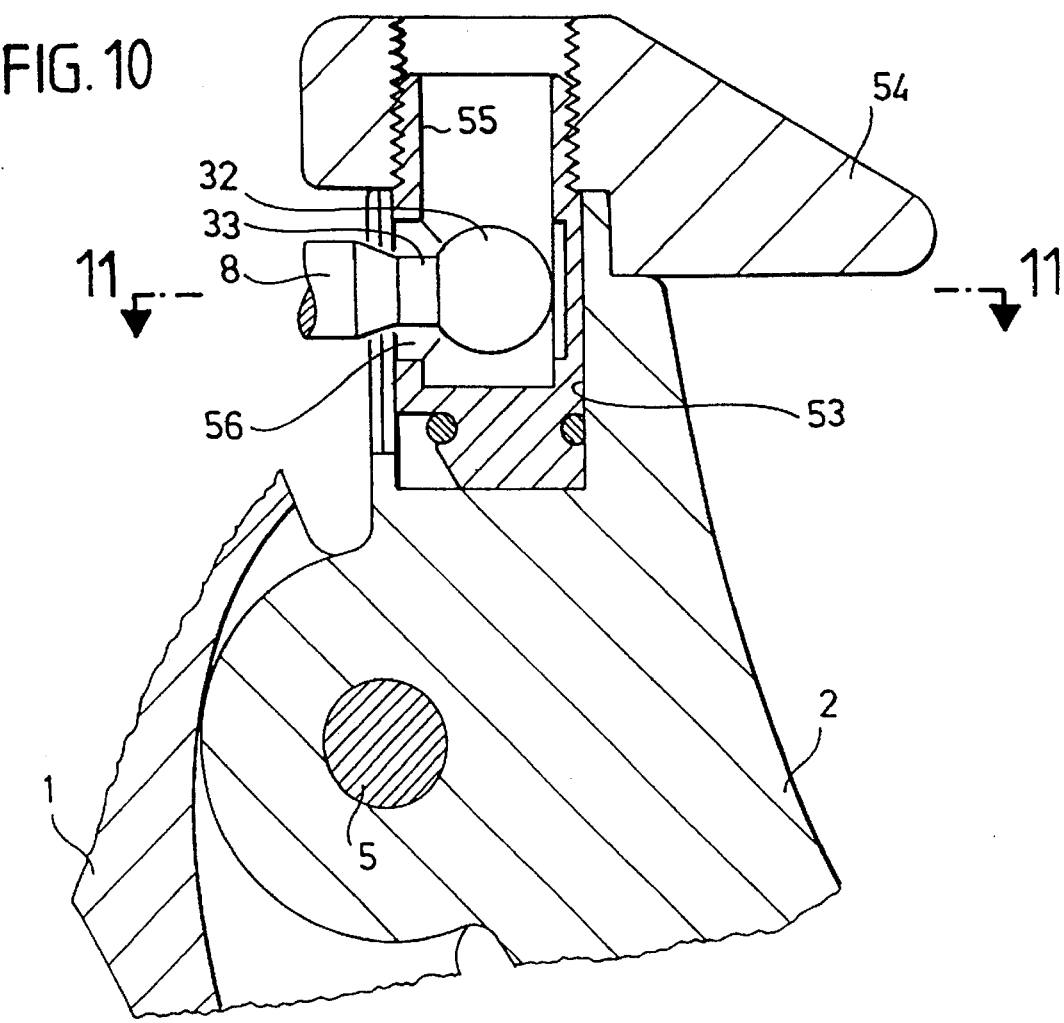
FIG. 10 a view similar to FIG. 4 of a modified embodiment of a pivotable retaining member.
Figure 11:
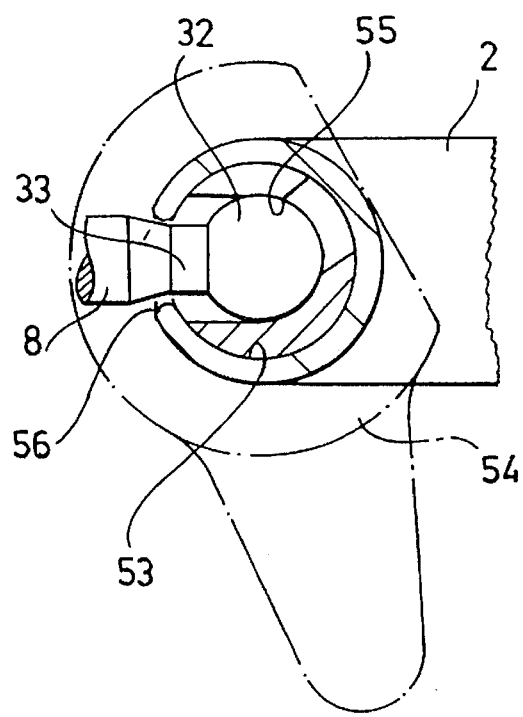
FIG. 11 a sectional view along line 11—11 in FIG. 10.

In the embodiment of FIGS. 10 and 11 there is inserted in a vertical bore 53 of the handle part 2 a swivel body 54 which is rotatable about the vertical axis of the bore 53. Arranged in the swivel body 54 coaxially with the bore 53 is a blind hole bore 55 which communicates with the outer space via a transversely arranged keyhole-shaped opening 56. In a first position, the narrow region of the keyhole-shaped opening 56 is arranged in the longitudinal direction of the actuating element 8 so that the larger spherical end 32 is prevented from exiting; in the other end position, however, the larger part of the keyhole-shaped opening 56 is arranged in this direction and so in this position the spherical end 32 can exit from the opening 56. In this embodiment, too, the swivel body 54 rotatable, in this case, about the vertical axis, could be fixed by detent members in the end positions. This is not shown expressly in the drawings.

In each case, when assembling the described instrument, the holder 9 with the tool 7 is first pushed into the front end of the tube 13 until the tongues 16 snap into the circumferential groove 15. The actuating element 8 permanently connected to the tool 7 is thereby guided through the bore 31, and the free end of the actuating element 8 protrudes at the rear side of the tube 13 beyond the latter.

To fix the connection between tool 7 and tube 13, the outer tube 17 can be displaced such that it covers the tongues 16. This unit is then pushed into the tubular receptacle 18, and the sleeve 24 is simultaneously displaced against the action of the helical spring 26. Unimpeded entry of the tube 13 into the receptacle 18 is thereby made possible, without the ball 22 preventing this entering movement. When the tube 13 is pushed in, the projection 20 enters one of the longitudinal slots 19 and thereby aligns the tube into the desired angular position in the circumferential direction. Once the desired push-in depth is reached, the sleeve 24 is released so it moves into the closed position under the action of the helical spring 26 and thereby pushes the ball 22 into the aligned recess 23 of the tube 13. The tube 13 is thereby fixed in the axial direction in the receptacle. This also results in a fixing of the outer tube 17 on the tube 13, and so the tool 7 is now also permanently locked in the tube 6.

During this pushing-in movement of the tube 13, the spherical end 32 of the actuating element 8 has entered the retaining member which is in the open position. By moving the retaining member into the closed position, the spherical end 32 is partly articulatedly surrounded by the retaining member, and, in addition, the end 32 is prevented from being displaced in the direction of the actuating element 8. Pulling and pushing forces can thus be transmitted from the handle part 2 to the actuating element 8.

In order to disassemble the instrument, the procedure is carried out in reverse order.

We claim:

1. A tubular-shafted surgical instrument comprising:

two handle parts articulatedly connected to each other, a tube held on one handle part, a tool releasably mounted at an end of said tube, a rod-shaped actuating element for said tool, said actuating element being mounted for longitudinal displacement in said tube and being articulatedly connected to said other handle part via a cylindrical or spherical end, a releasable connection between said tube and actuating element being releasably connected to said two handle parts, said tube being pushable into a tubular receptacle on said one handle part and axially fixable therein by at least one radially moveable locking body which in an end position enters into a positive connection with said tube, and a retaining member being mounted on said other handle part, said retaining member at least partly embracing said cylindrical or spherical end of said actuating element in one end position and being moveable into another end position in which said cylindrical or spherical end is removable from said other handle part in the longitudinal direction, wherein:

said locking body is a ball, said radial movement of said locking body is delimited by a stop resting against the outer side of said locking body, said stop being formed by a sleeve axially displaceable on said tubular receptacle, said sleeve is displaceable relative to said locking body such that said locking body is radially outwardly displaceable to different extents, said sleeve forms a stop for an outer tube which is mounted for axial displacement on said tube, where said sleeve in a forward end position locks the releasable mounting of said tool at the opposite end of said tube, and said sleeve is displaceable in the direction towards said handle parts in order to release the locking of said tube.

2. An instrument as defined in claim 1, wherein said sleeve is displaced in a spring-loaded manner into said end position in which the path of displacement of said locking body is limited to the greatest extent.

3. An instrument as defined in claim 2, wherein said tubular receptacle forms a stop for an outer tube which is mounted for axial displacement on said tube and in the pushed forward end position locks the releasable mounting of said tool at the opposite end of said tube.

4. An instrument as defined in claim 3, wherein said retaining member is mounted for swivel movement on said other handle part and in the closed state engages in a section of said actuating element adjacent to said spherical or cylindrical end, the outer dimensions of said section transversely to the longitudinal direction of said actuating element being smaller than those of said spherical or cylindrical end.

5. An instrument as defined in claim 4, wherein said retaining member has a receiving space for said spherical or cylindrical end with an opening which has a larger region sufficient for passage of said spherical or cylindrical end therethrough and a smaller region which is too narrow for passage therethrough, and in that by movement of said retaining member, said two regions are selectively moveable in the longitudinal direction of said actuating element in front of its spherical or cylindrical end.

6. An instrument as defined in claim 2, wherein said retaining member is mounted for swivel movement on said other handle part and in the closed state engages in a section of said actuating element adjacent to said spherical or cylindrical end, the outer dimensions of said section transversely to the longitudinal direction of said actuating element being smaller than those of said spherical or cylindrical end.

7. An instrument as defined in claim 6, wherein said retaining member has a receiving space for said spherical or cylindrical end with an opening which has a larger region sufficient for passage of said spherical or cylindrical end therethrough and a smaller region which is too narrow for passage therethrough, and in that by movement of said retaining member, said two regions are selectively moveable in the longitudinal direction of said actuating element in front of its spherical or cylindrical end.

8. An instrument as defined in claim 1, wherein said tubular receptacle forms a stop for an outer tube which is mounted for axial displacement on said tube and in the pushed forward end position locks the releasable mounting of said tool at the opposite end of said tube.

9. An instrument as defined in claim 8, wherein said retaining member is mounted for swivel movement on said other handle part and in the closed state engages in a section of said actuating element adjacent to said spherical or cylindrical end, the outer dimensions of said section transversely to the longitudinal direction of said actuating element being smaller than those of said spherical or cylindrical end.

10. An instrument as defined in claim 9, wherein said retaining member has a receiving space for said spherical or cylindrical end with an opening which has a larger region sufficient for passage of said spherical or cylindrical end therethrough and a smaller region which is too narrow for passage therethrough, and in that by movement of said retaining member, said two regions are selectively moveable in the longitudinal direction of said actuating element in front of its spherical or cylindrical end.

11. An instrument as defined in claim 1, wherein said tube is secured against rotation about the longitudinal axis of said tube by engagement of projections and recesses when pushed into said tubular receptacle.

12. An instrument as defined in claim 11, wherein said projections and recesses are adapted to engage in different angular positions.

13. An instrument as defined in claim 1, wherein said tubular receptacle is mounted for rotation about its longitudinal axis on said handle part.

14. An instrument as defined in claim 1, wherein said retaining member is constructed as a collet chuck which in the released state allows entry or exit of said spherical or cylindrical end by bending open elastically and in the closed state embraces the latter unreleasably.

15. An instrument as defined in claim 1, wherein said retaining member is mounted for swivel movement on said other handle part and in the closed state engages in a section of said actuating element adjacent to said spherical or cylindrical end, the outer dimensions of said section transversely to the longitudinal direction of said actuating element being smaller than those of said spherical or cylindrical end.

16. An instrument as defined in claim 15, wherein said retaining member has a receiving space for said spherical or cylindrical end with an opening which has a larger region sufficient for passage of said spherical or cylindrical end therethrough and a smaller region which is too narrow for passage therethrough, and in that by movement of said retaining member, said two regions are selectively moveable in the longitudinal direction of said actuating element in front of its spherical or cylindrical end.

17. An instrument as defined in claim 16, wherein said retaining member is positionable in its end positions by elastic detent members.

18. An instrument as defined in claim 17, wherein said opening comprises a keyhole-shaped design.

* * * * *